(12) United States Patent
Can et al.

(10) Patent No.: US 8,789,626 B2
(45) Date of Patent: Jul. 29, 2014

(54) ULTRA HARD/HARD COMPOSITE MATERIALS

(76) Inventors: Antionette Can, Springs (ZA); Geoffrey John Davies, Springs (ZA); Johannes Lodewikus Myburgh, Springs (ZA)

( * ) Notice: Subject to any disclaimer, the term of this patent is extended or adjusted under 35 U.S.C. 154(b) by 420 days.

(21) Appl. No.: 13/141,042

(22) PCT Filed: Dec. 18, 2009

(86) PCT No.: PCT/IB2009/055836
§ 371 (c)(1),
(2), (4) Date: Aug. 3, 2011

(87) PCT Pub. No.: WO2010/073198
PCT Pub. Date: Jul. 1, 2010

(65) Prior Publication Data
US 2011/0297450 A1  Dec. 8, 2011

(30) Foreign Application Priority Data

Dec. 22, 2008 (GB) .................................. 0823328.0

(51) Int. Cl.
*E21B 10/46* (2006.01)
(52) U.S. Cl.
USPC .......................................... 175/428; 175/434
(58) Field of Classification Search
USPC ........................................ 175/374, 428, 434
See application file for complete search history.

(56) References Cited

U.S. PATENT DOCUMENTS

| 3,841,852 | A | 10/1974 | Wilder et al. | |
| 8,020,643 | B2 * | 9/2011 | Russell et al. | 175/433 |
| 2003/0224220 | A1 | 12/2003 | Nguyen et al. | |
| 2005/0139397 | A1 | 6/2005 | Achilles et al. | |
| 2006/0057287 | A1 | 3/2006 | Foss et al. | |
| 2006/0112854 | A1 | 6/2006 | Leu | |
| 2006/0154800 | A1 | 7/2006 | Chen | |
| 2010/0122852 | A1 * | 5/2010 | Russell et al. | 175/428 |

FOREIGN PATENT DOCUMENTS

| EP | 0698447 | A2 | 2/1996 |
| EP | 1043293 | A1 | 11/2000 |
| GB | 2362655 | A | 11/2001 |
| JP | 63035456 | A | 2/1988 |
| JP | 63303029 | A | 12/1988 |
| JP | 07-188827 | | 7/1995 |
| JP | 02282443 | | 2/2002 |
| JP | 02282444 | | 2/2002 |
| JP | 04026554 | | 1/2004 |
| WO | 2006032984 | A2 | 3/2006 |
| WO | 2007144731 | A2 | 12/2007 |
| WO | 2007144733 | A2 | 12/2007 |
| WO | 2007148214 | A2 | 12/2007 |

OTHER PUBLICATIONS

Patent Cooperation Treaty Search Report for PCT/IB2009/055836 dated May 12, 2010.
Selsing, Jorgen, Internal stresses in ceramics, Journal of the American Ceramics Society, Aug. 1961, 419, 44 (8), doi: 10.1111/j.1151-2916.1961.tb15475.x.
Cannon, John Francis, Behavior of the elements at high pressures, Journal of Physical and Chemical Reference Data, Jul. 1974, 780-824, 3(3), doi: 10.1063/1.3253148.

* cited by examiner

*Primary Examiner* — William P Neuder
(74) *Attorney, Agent, or Firm* — Bryan Cave LLP

(57) ABSTRACT

The invention provides for an ultra hard or hard composite material comprising a primary ultra hard or hard particulate material and at least one secondary ultra hard or hard particulate material dispersed in a matrix material. The primary ultra hard or hard particulate material has a thermal expansion coefficient lower than that of the matrix material and the at least one secondary ultra hard or hard particulate material has a thermal expansion coefficient greater than that of the matrix material.

19 Claims, No Drawings

ULTRA HARD/HARD COMPOSITE MATERIALS

BACKGROUND OF THE INVENTION

This invention relates to ultra hard or hard composite materials, and to methods of making them.

Ultra hard composite materials, typically in the form of abrasive compacts, are used extensively in cutting, milling, grinding, drilling and other abrasive operations. They generally contain ultra hard abrasive particles dispersed in a second phase matrix. The matrix may be metallic or ceramic or a cermet. The ultra hard or hard abrasive particles may be diamond, cubic boron nitride (cBN), silicon carbide or silicon nitride and the like. These particles may be bonded to each other during the high pressure and high temperature compact manufacturing process generally used, forming a polycrystalline mass, or may be bonded via the matrix of second phase material(s) to form a polycrystalline mass. Such bodies are generally known as polycrystalline diamond (PCD), or polycrystalline cubic boron nitride (PCBN), where they contain diamond or cBN as the ultra hard particles, respectively.

PCT application WO2006/032984 discloses a method of manufacturing a polycrystalline abrasive element, which includes the steps of providing a plurality of ultra hard abrasive particles having vitreophilic surfaces, coating the ultra hard abrasive particles with a matrix precursor material, treating the coated ultra hard abrasive particles to render them suitable for sintering, preferably to convert the matrix precursor material to an oxide, nitride, carbide, oxynitride, oxycarbide, or carbonitride of the matrix precursor material, or an elemental form of the matrix precursor material, or combinations thereof, and consolidating and sintering the coated ultra hard abrasive particles at a pressure and temperature at which they are crystallographically or thermodynamically stable. In this way ultra hard polycrystalline composite materials are made having ultra hard particles homogeneously dispersed in fine, sub-micron and nano grained matrix materials.

The ultra hard abrasive elements typically comprise a mass of ultra hard particulate materials of any size or size distribution smaller than about several hundred microns, down to and including sub-micron and also nano-sizes (particles less than 0.1 microns i.e. 100 nm), which are well dispersed in a continuous matrix made of extremely fine grained oxide ceramics, non-oxide ceramics, cermets or combinations of these classes of materials.

EP 0 698 447 discloses another approach to the generation of ultra hard composite materials, whereby the matrix is generated by the pyrolysis of organometallic polymer precursors, such as pyrolysis of polymerized polysilazanes. This has particular utility for the generation of ultra hard composites derived from diamond and/or cBN where the ceramic matrices are selected from silicon carbide, silicon nitride, silicon carbonitride, silicon dioxide, boron carbide, aluminium nitride, tungsten carbide, titanium nitride, and titanium carbide.

SUMMARY OF THE INVENTION

According to the invention there is provided an ultra hard or hard composite material comprising a primary ultra hard or hard particulate material and at least one secondary ultra hard or hard particulate material dispersed in a matrix material, characterized in that the primary ultra hard or hard particulate material has a thermal expansion coefficient lower than that of the matrix material and the at least one secondary ultra hard or hard particulate material has a thermal expansion coefficient greater than that of the matrix material.

The invention extends to an abrasive insert which comprises a layer of PCD or PCBN; a cemented carbide substrate to which the layer of PCD or PCBN is bonded through an interlayer; the interlayer comprising a composite material as described above.

DETAILED DESCRIPTION OF PREFERRED EMBODIMENTS

This invention concerns ultra hard or hard composite materials consisting of more than one type of ultra hard or hard particulate material bonded in a common, continuous matrix material.

According to the invention, primary ultra hard or hard particulate material having a thermal expansion coefficient lower than that of the matrix material is introduced into the matrix material together with at least one type of secondary ultra hard or hard particulate material, at least one of which has a thermal expansion coefficient greater than that of the matrix material.

In the case of a single type of secondary ultra hard or hard particulate material, $\alpha_p$, $\alpha_m$ and $\alpha_s$ represent the thermal expansion coefficients at room temperature (25° C.) of the primary particles, matrix material and the secondary particles, respectively.

This aspect of the invention may then be summarized as a composite material containing distinct primary and secondary particulate material dispersed in a matrix, whereby the materials are chosen such that the following relationship holds:

$$\alpha_p < \alpha_m < \alpha_s \qquad (1)$$

It is known that when particles in a matrix have a thermal expansion coefficient lower than the matrix in which they are bonded, tensile stress fields are set up in the matrix and the particles are under compression.

Conversely when particles in a matrix have a thermal expansion coefficient greater than the matrix in which they are bonded, compressive stress fields are set up in the matrix and the particles themselves are under tension.

When two types of particulate materials (designated as primary and secondary particles) are present in the same matrix, whereby the thermal expansion coefficients of the three material components hold to equation (1), then it is to be expected that the stress fields surrounding the particles of the two different particulate materials, primary and secondary, will to a lesser or greater extent tend to cancel each other out. In this way by choice of the primary and secondary particulate materials, their size distributions and concentrations, and choice of the matrix material, the stress field distributions in the matrix may be optimally engineered. The objective of the designed and engineered stress fields, at the scale of the particulate material in the composite, is to have the ability to affect and optimize the resultant thermo mechanical properties of the composite material. Subsequently, optimized and improved composite materials for a large scope of diverse applications may then be approached.

The best control over the average stress fields, at the scale of the particulate material in the composite, will result if the primary and secondary particles are homogeneously distributed in space in the matrix, such that each primary particle is in the environs of secondary particles and vice versa. The engineering of the stress fields in the matrix in this manner is an aspect of the present invention.

Another aspect of the invention is where more than one type of secondary particulate material is employed and bonded together with primary particulate material at high temperature into chosen, compatible matrices. The primary and more than one type of secondary particles are chosen with respect to their relative thermal expansion coefficients and that of the chosen matrix material.

A general expression of this aspect of the invention may be provided where $\alpha_p$ is the thermal expansion coefficient of the primary particles in the matrix and it is always less than that of the matrix, $\alpha_m$. Now taking the number of types of secondary particulate material to be n, where n may be any integer greater than 1. The different types of secondary particulate materials may have thermal expansion coefficients less than or greater than that of the matrix. The number of secondary particulate materials with thermal expansion coefficients greater than that of the matrix is x, where x is 1 or more and is less than or equal to n.

Then the general expression of the invention for a primary particulate material incorporated into a matrix with n secondary types of particulate material is:

$$\alpha_p \text{ to } \alpha_{n-x} < \alpha_m < \alpha_x \quad (2)$$

The invention therefore encompasses composite materials where the primary particulate material has a thermal expansion coefficient always less than that of the matrix, together with the presence of any number of types of secondary particulate materials, all or any number of which have thermal expansion coefficients greater than that of the matrix, provided that at least one of them fulfills this requirement.

The primary particulate materials include ultra hard and hard particles such as diamond, cubic boron nitride, silicon carbide, silicon nitride, sialons, boron carbide, alumina and the like. More generally any compound or material with desired mechanical properties and chemical compatibility with the matrix material of choice, including oxide and non-oxide ceramics, metals and cermets, may be used.

The matrix materials include ceramics such as metal oxides, nitrides, carbides, borides and in particular those matrices disclosed in EP 0 698 447, PCT application WO2006/032984, EP 0 7766525, EP 0 7789413 and PCT publication WO2007/148214, incorporated herein by reference. In particular the invention includes nano grain sized, that is less than 100 nm grain sized, versions of these disclosed matrix types. The matrices also include metals such as tungsten, molybdenum and similar high melting point metals and alloys.

The secondary particulate materials include single crystalline and polycrystalline ceramics, metals, alloys and cermets.

The average grain size of the primary and secondary particulate materials may be within the ranges of 10 to 100 microns, 1 to 10 microns, 0.1 to 1 micron (sub-micron), less than 0.1 micron (nano sized) i.e. less than 100 nm.

The primary particles may be smaller than or larger than the secondary particles.

Preferably the primary and secondary particles will be similar or of equal size.

The relative sizes of each particulate material component of the overall composite material may be chosen to engineer and manipulate the stress fields in the environs of the particles in the matrix.

The relative mass or volume ratios of the particulate material components of the overall composite material may also be chosen to engineer and manipulate the stress fields in the environs of the particles in the matrix.

A model mathematically describing the relationships between the spatial stress fields in the matrix and the size and properties of the particulate materials is given below. This model may be used as a guide to the design of preferred composite material embodiments, which are encompassed by the scope of the present invention.

The ultra hard composite materials, typically formed as polycrystalline abrasive bodies, also referred to as polycrystalline abrasive elements, are used as cutting tools for turning, milling and honing, drilling cutters for rock, ceramics and metals, wear parts and the like. Bio-compatible versions of composite materials may also be used in load bearing prosthetic applications.

The invention is particularly directed to tailoring the thermal expansion coefficient mismatches of the components of the composite materials, where the material phases present are micron, sub-micron and/or nano-grain sized, so that the expected improvements in properties and behavior in applications as a result of the use of such material phases can be exploited.

The ultra hard composite materials may be generated by the sintering of the matrix material at high temperature and pressure. Alternatively other appropriate consolidation and sintering technologies such as spark plasma sintering (SPS) may also be employed.

At the high temperature conditions used in these sintering technologies, the ultra hard or hard particulate materials and matrix materials reach elastic, plastic equilibrium with each other after sintering and thus there will be an absence of local stress, provided the high temperature and pressure conditions are maintained.

On cooling to room temperature, however, differences in thermal expansion coefficient between the ultra hard or hard particulate materials and the matrix will generate local stresses at the scale of said particles and the matrix microstructure.

It is known in the literature that the thermal expansion mismatch stress, $\sigma_T$ inside a single spherical particle in an infinite matrix may be expressed by the so called Selsing formula, (J. Selsing; "Internal Sresses in Ceramics"; J. Am. Ceram. Soc., 1961, vol.44, p 419.):

$$\sigma_T = \Delta\alpha\Delta T/\Gamma \quad (3)$$

$$\text{where } \Delta\alpha = \alpha_p - \alpha_m \quad (4)$$

which is the difference in thermal expansion coefficient between a primary particle material, $\alpha_p$ and that of the matrix material, $\alpha_m$;

$$\text{where } \Delta T = T_{pl} - T_{room} \quad (5)$$

which is the difference between the elastic, plastic transition temperature of the matrix material, $T_{pl}$ and room temperature, $T_{room}$; and $$\text{where } \Gamma = (1+\upsilon_m)/2E_m + (1-2\upsilon p)/Ep \quad (6)$$

where $\upsilon$ is Poisson's ratio, E is Young's modulus, and the subscripts m and p denote matrix and primary particle, respectively.

The tangential, $\sigma_{Tt}$, and radial, $\alpha_{Tr}$, stress distributions in the matrix around the particle may be given by:

$$\sigma_{Tt} = -(\sigma_T/2)(r_p/x)^3 \quad (7)$$

$$\text{and } \sigma_{Tr} = \sigma_T(r_p/x)^3 \quad (8)$$

where $r_p$ denotes the radius of the particle and x is the radial distance from the particle.

In the case where $\alpha_p$ is less than $\alpha_m$ as was defined above for the primary particulate material, the average residual stresses after cooling are compressive in the primary particles and tensile in the matrix.

In the case where a secondary particulate material of thermal expansion coefficient $\alpha_s$ is present and where $\alpha_s$ is greater than $\alpha_m$, the average residual stresses resulting after cooling are tensile in the secondary particles and compressive in the matrix in the environs of said secondary particles.

Again the residual stress field in the matrix dependence upon the particle radius r, and distance from the particle into the matrix x, is of the form of equations (7) and (8) above, but of the opposite sense, that is compressive.

Where a primary and secondary particle are in close proximity in a matrix, that is separated by a distance of similar magnitude to their diameters, and the thermal expansion coefficients are as expressed in equation (1), then the resultant stress field in the matrix between them will be reduced as a result of the partial cancellation of the tensile and compressive stress fields associated with the differing particles.

The magnitude of the resultant, residual local stress fields in a matrix, at the scale of the component particles will thus be dependent not only upon the materials of the primary and secondary particles, but upon their relative sizes, concentrations, and homogeneity with respect to each other in the matrix.

The invention is used to best effect when the homogeneity is of a high degree, such that each primary particle will be in the environs of a significant number of secondary particles with an appropriate proximity between them.

When the primary and secondary particulate materials are of comparable size, the desired high degree of homogeneity results when the ratio of volume percentage compositions of the primary to secondary particulate components is between 1 to 2 and 2 to 1. This means that the ratio of the number of primary to secondary particles per unit volume of composite material is between 1 to 2 and 2 to 1. An even more preferred embodiment is where the number of primary and secondary particles per unit volume in the composite material is substantially equal.

The stress field spatial distribution in the matrix may thus be manipulated and reduced, which will have consequences for crack initiation and propagation in the material and so significantly influence the behavior of the material when it is used in thermo-mechanical applications, where it may be subjected to severe conditions.

Table 1 is an exemplary and a non-comprehensive list of hard and ultra hard ceramic materials with their linear thermal expansion coefficients, which may be used in this invention.

TABLE 1

| Ceramic Material | Thermal expansion Coefficient (ppm/° K |
|---|---|
| Diamond | 0.8 |
| cBN | 1.0 |
| CrN | 2.3 |
| $Si_3N_4$ | 3.2 |
| TaN | 3.6 |
| SiC | 4.4 |
| $B_4C$ | 4.5 |
| AlN | 5.7 |
| WC | 6.0 |
| TaC | 6.3 |
| $Cr_2O_3$ | 6.7 |
| ZrC | 6.7 |
| HfC | 6.9 |
| HfN | 6.9 |
| NbC | 7.2 |
| ZrN | 7.2 |
| VC | 7.3 |
| TiC | 7.4 |
| $Mo_2C$ | 7.8 |

TABLE 1-continued

| Ceramic Material | Thermal expansion Coefficient (ppm/° K |
|---|---|
| VN | 8.1 |
| $Al_2O_3$ | 8.4 |
| TiN | 9.4 |
| $ZrO_2$ | 10.0 |
| NbN | 10.1 |
| $Cr_3C_2$ | 10.4 |

Table 2 is an exemplary and non-comprehensive list of the thermal expansion coefficients of elemental metals and some key metal alloy types, together with some melting points at room pressure and 5.5 GPa, where appropriate, which may be used in this invention. The thermal expansion coefficients given for metal elements are for room temperature, whereas those for the alloy types are for a temperature range of 540 to 980° C.

The high pressure melting points were taken from J. F Cannon, J. Phys. Chem. Ref. Data, Vol3, No. 3, 1974.

TABLE 2

| Metal Material | Thermal expansion Coefficient (ppm/° C.) | Melting Point (° C.) | Melting Point at 5.5 GPa (° C.) |
|---|---|---|---|
| W | 4.5 | 3422 | 3750 |
| Mo | 4.8 | 2623 | 2650 |
| Cr | 4.9 | 1907 | |
| Zr | 5.7 | 1855 | |
| Hf | 5.9 | 2233 | |
| Ta | 6.3 | 3017 | 3250 |
| Nb | 7.3 | 2477 | |
| V | 8.4 | 1910 | |
| Ti | 8.6 | 1668 | |
| Pt | 8.8 | 1768 | 2030 |
| Pd | 11.8 | 1555 | |
| Fe | 11.8 | 1538 | 1700 |
| Co | 13.0 | 1495 | |
| Ni | 13.5 | 1455 | 1650 |
| Stainless Steels | 11 to 19 | — | — |
| Alloy Steels | 11 to 15 | — | — |
| Co based superalloys | 12 to 17 | — | — |
| Ni based superalloys | 14 to 18 | — | — |
| Au | 14.2 | 1064 | 1350 |
| Cu | 16.5 | 1085 | 1270 |
| Ag | 18.9 | 962 | 1250 |

Table 3 is an exemplary and a non-comprehensive list of the thermal expansion coefficients of cermet types, which may be used in this invention. The thermal expansion coefficients given are for room temperature.

TABLE 3

| Cermet | Thermal expansion Coefficient (ppm/° C.) |
|---|---|
| Tungsten Carbide based | 4 to 7 |
| Alumina based | 8 to 9 |
| Chromium Carbide based | 10 to 11 |
| Titanium Carbide based | 8 to 13 |

High melting point, congruent melting intermetallic compounds such as $Ni_3Ti$ (mp=1380° C.), $Ni_3Al$ (mp=1385° C.), $Ni_3Ta$ (mp=1550° C.), AlNi (mp=1638° C.) and many others are also candidates for primary and secondary particulate components for the composite materials of the present invention.

Tables and lists of this nature may be used to select primary and secondary particulate materials and matrix materials to be combined to form composite materials indicated by aspects of the present invention, that is, to comply with the thermal expansion conditions expressed by equations (1) or (2) above.

Ultra hard composite materials which often utilize ultra hard particulate materials such as diamond and cubic boron nitride (cBN), are particularly likely to suffer from residual stress problems due to tensile stress fields in the matrices. This is because, as may be seen from Table 1, diamond and cBN have very low thermal expansion coefficients (about 1 ppm/° C. at room temperature) as compared to the candidate materials for the matrix materials. Depending upon the method of composite fabrication and the attendant conditions of consolidation and sintering, many of the materials listed in Tables 1, 2 and 3 are candidates for matrix materials. As compared to diamond and cBN some of these materials have very large thermal expansion coefficients, with thus very large room temperature thermal expansion mismatches. These large thermal expansion mismatches can lead to very large tensile stress fields in the matrices which may in some cases be so large that they can potentially lead to spontaneous micro cracking on cooling and render the desired composite material either very difficult or even impossible to produce as useful macroscopic pieces. By reference to equations (7) and (8), it may be seen that this is expected to be particularly prevalent as diamond or cBN particles of larger than a few microns are utilized. This is because the tensile stress field intensity is dependent upon the third power of the radius of the particle. Thus, the larger the particle, the greater the tensile stress intensity in the matrix.

An example of the case fulfilling equation 1, is where diamond or cBN is desired to be bonded in a titanium nitride matrix. By reference to Table 1, it may be seen that the coefficient of thermal expansion of titanium nitride (TiN) is $9.4 \times 10^{-6}$/° C. (9.4 ppm/° C.), so the thermal expansion coefficient difference to that of diamond or cBN is large at about 8.4 ppm/° C. This large difference is expected to give rise to large tensile stress fields in the TiN matrix. These large stress fields may under some circumstances be advantageous, for example where they provide for preferential crack propagation paths. However, it is also advantageous to modify and reduce the tensile stress fields in the TiN matrix by the introduction of a secondary hard particle with thermal expansion coefficient greater than that of TiN.

By reference to Table 1, it may be seen that chromium carbide ($Cr_3C_2$) has a thermal expansion coefficient of 10.4 ppm/° C. This is significantly larger than that of TiN. Moreover, $Cr_3C_2$ particles are expected to be chemically compatible with the known process(es) and methods required to produce the composite material. $Cr_3C_2$ thus is a candidate for a secondary hard particle for exploitation in this invention as it clearly fulfills the requirement as expressed by equation (1). Thus composite materials comprising diamond or cBN as primary particles, titanium nitride (TiN) as matrix and chromium carbide as secondary particles are embodiments of the present invention and are exemplary in that regard.

Preferred versions of this embodiment use nano grain sized (less than 100 nm) titanium nitride (TiN) matrices. More preferable versions of this embodiment use nano grained TiN matrices where the grain size of the matrix is at or close to the Hall Petch departure value for TiN, namely 50 nm, as disclosed in South African Patent Application 2006/04765.

By reference to Table 2, it may also be seen that many of the metals listed have thermal expansion coefficients greater than that of matrix materials such as TiN and the like listed in Table 1. However not all of them may be compatible with the methods and processes exploitable to make diamond and cBN in such matrices.

In general, if any metal is intended for use as a secondary particle in any embodiment of the present invention, it must not melt and must remain as a coherent particulate component of the composite material during the fabrication procedures and methods of manufacture of the composite.

Some important key methods to produce composite materials with ceramic matrices known in the art exploit chemical precursor approaches to generate the ceramic or glass ceramic matrices. Examples of such methods are disclosed in EP 0 698 447, PCT application WO2006/032984, EP 0 7766525, EP 0 7789413 and PCT publication WO2007/148214. These methods in general make use of the phenomenon that nano-grain sized materials derived from precursor chemicals are sinterable at low temperatures, sometimes at temperatures as much as 500° C. lower than conventional sintering temperatures for already existing micron sized crystalline material particles.

The nano grain sized matrices preferred in the present invention are sinterable in the range of 900 to 1450° C., particularly if the sintering is carried out at high pressures, such as 5.5 GPa, for example. The melting point of most metals is elevated by the application of pressure due to the normal behavior of expansion of the metal at melting. Typical average elevations of transition metal melting points such as for cobalt, nickel and iron are about 30 to 40° C. per GPa. Thus for example, as shown in Table 2, the melting point of pure nickel (Ni) at 5.5 GPa is close to 1650° C. It has been determined that an appropriate sintering temperature for nano grain sized $Al_2O_3$ and TiN at 5.5 GPa is in the range 1350 to 1450° C. At these conditions particles of pure Ni will not melt and will remain as coherent particles in the sintering matrices.

The thermal expansion coefficient of Ni at room temperature is 13.5 ppm/° C., thus Ni may be used as an efficient secondary particle in such matrices where diamond and or cBN are used as primary particles. Composite materials of this embodiment of the invention are provided where the thermal expansion of the primary particles (diamond and cBN at about 1 ppm/° C.) is significantly less than the matrix materials ($Al_2O_3$ at 8.4 and TiN at 9.4 ppm/° C., respectively), which are in turn significantly less than the secondary particle material (Ni at 13.5 ppm/° C.).

A further example of the case fulfilling equation 1, is where diamond is desired to be bonded in a tantalum carbide matrix. By reference to Table 1, it may be seen that the coefficient of thermal expansion of tantalum carbide (TaC) is $6.3 \times 10^{-6}$/° C. (6.3 ppm/° C.), so the thermal expansion coefficient difference to that of diamond or cBN is large at about 5.5 ppm/° C. This significant difference in thermal expansion coefficient is expected to give rise to large tensile stress fields in the TaC matrix. These large stress fields may under some circumstances be advantageous, for example where they provide for preferential crack propagation paths. However, it is also advantageous to modify and reduce the tensile stress fields in the TaC matrix by the introduction of a secondary hard particle with thermal expansion coefficient greater than that of TaC.

By reference to Table 1, it may be seen that aluminium oxide ($Al_2O_3$) has a thermal expansion coefficient of 8.4 ppm/° C. This is significantly larger than that of TaC. $Al_2O_3$ thus is a candidate for a secondary hard particle for exploitation in this invention as it clearly fulfills the requirement as expressed by equation (1). Thus composite materials comprising diamond as primary particles, tantalum carbide (TaC) as matrix and aluminium oxide as secondary particles are embodiments of the present invention and are exemplary in that regard. Preferred versions of this embodiment use nano grain sized (less than 100 nm) tantalum carbide (TaC) matrices.

Thus, generally, metal particulate materials which are compatible with the chosen matrix material in regard to viable sintering and fabrication methods for said matrix, and are able to remain as coherent, unmelted particles can be used as secondary particles in embodiments of the present invention, provided of course at least one of them has a thermal expansion coefficient greater than that of the matrix. Table 2, is an exemplary and thus not comprehensive list of such particulate metals.

Of particular utility as metallic secondary particulate components of the composites of the present invention are the various types of superalloys, the thermal expansion coefficients of which are indicated in Table 2. Thus the well known, highly desirable thermo-mechanical general properties of superalloys, such as high temperature strength, can be brought to bear in embodiments of the present invention.

This may also be applied to general particulate cermet materials, some examples of which are listed in Table 3, as well as high melting point intermetallic compounds, which are also useful secondary particulate materials.

The invention further relates to abrasive inserts which comprise composite abrasive compacts. The abrasive inserts are characterized by an interlayer between the PCD or PCBN layer and the cemented carbide substrate. This interlayer comprises a composite material as described above.

The PCD or PCBN layer may be of fine grain or coarse grain type. The thickness will vary according to the nature and particle size of the layer.

The cemented carbide of the substrate may be any known in the art such as cemented tungsten carbide, cemented tantalum carbide, cemented molybdenum carbide or cemented titanium carbide. Such cemented carbides, as is known in the art, have a bonding phase such as nickel, cobalt, iron or alloys containing one or more of these metals. Typically, the bonding phase is present in the amount of 6 to 20% by mass. When the PCD or PCBN layer is a thick layer, it is preferred that the bonding phase of the cemented carbide is less than 8% by mass and preferably less than 6% by mass.

The abrasive insert may have any suitable shape, depending on the application to which it will be put. For example, the abrasive insert may have a disc shape with an upper flat working surface defining a cutting edge around its periphery. The invention has particular application to abrasive inserts which are shaped, e.g. where the superabrasive layer presents a bullet or dome shape which provides the working surface for the insert.

The abrasive insert of the invention may be made by a method which forms another aspect of the invention. The method includes the steps of:
(1) providing a cemented carbide substrate,
(2) placing a layer of the components necessary to produce an interlayer as described above on a surface of the cemented carbide substrate,
(3) placing a layer of diamond or cubic boron nitride particles, optionally with a suitable bonding phase material, on the layer of step (2), creating an unbonded mass, and
(4) subjecting the unbonded mass to elevated temperature and pressure at which the diamond or cubic boron nitride is crystallographically stable to produce a bonded abrasive insert.

The elevated temperature and pressure conditions which are applied are known in the art. They will be those necessary to produce PCD from a mass of diamond particles and PCBN from a mass of cubic boron nitride particles. Typically these conditions will be a temperature in the range 1300 to 1600 degrees centigrade and a pressure in the range 5 to 8 GPa.

The invention will now be described, by way of example only, with reference to the following non-limiting example.

EXAMPLE

In order to produce precompact sample, 406.3 g of $Ta(OC_2H_5)_5$ was first dissolved in 75 ml of dry ethanol in a dropping funnel A. 52 ml of deionised water was mixed with 50 ml of AR ethanol in a dropping funnel B.

70 g of synthetic diamond with an average grain size of 1.5 micron was dispersed in 750 ml of AR ethanol using a high energy ultrasonic probe. Solutions from dropping funnels A & B were simultaneously fed into the beaker containing the diamond suspension, which was being stirred using a Silverson mechanical mixer.

After addition of all reagents, the resultant solution was dried in a rotavapour, followed by additional drying in an oven at 80° C. for 24 hours. The tantalum oxide coated diamond was than heat treated at 1300° C. in $H_2$/Ar gas mixture for 3 hours. X-ray diffraction analysis confirmed that the resultant powder was TaC coated diamond.

The 10 vol % TaC coated diamond powder was suspended in 1.5 liters of AR ethanol. 20 vol % submicron $Al_2O_3$ powder was added and mixed for 10 minutes, followed by the addition of 10 vol % 1 micron TaC powder, followed by 20 minutes of mechanical stirrer mixing.

This suspension was then dried in a rotavapour, followed by oven drying at 90° C. for 24 hours.

The diamond/alumina material dispersed in 20 vol % nano TaC precompact sample was analysed and showed a good homogeneous distribution of the diamond and alumina particles in the TaC matrix. Accordingly, it is believed that sintering of the precompact at 5.5 GPa and 1400° C. for about 15 minutes in a high pressure belt system would yield a solid structure (with no cracking) of about 1.5 micron average diamond grain size; 20 vol % submicron alumina material dispersed in 20 vol % nano TaC.

The invention claimed is:

1. An ultra hard or hard composite material comprising a primary ultra hard or hard particulate material and at least one secondary ultra hard or hard particulate material dispersed in a matrix material;
    wherein the primary ultra hard or hard particulate material has a thermal expansion coefficient lower than that of the matrix material and the at least one secondary ultra hard or hard particulate material has a thermal expansion coefficient greater than that of the matrix material; and
    wherein the primary ultra hard or hard particulate material is selected from the group of ultra hard and hard particles including diamond, cubic boron nitride, silicon carbide, silicon nitride, sialons, boron carbide, and alumina.

2. A composite material according to claim 1, wherein the composite material comprises a single secondary ultra hard or hard particulate material.

3. A composite material according to claim 1, wherein the composite material comprises more than one secondary ultra hard or hard particulate material.

4. A composite material according to claim 1, wherein the at least one secondary ultra hard or hard particulate material is selected from the group comprising single crystalline and polycrystalline ceramics, metals, alloys and cermets.

5. A composite material according to claim 1, wherein the matrix material is selected from the group of ceramics including metal oxides, nitrides, carbides and borides.

6. A composite material according to claim 1, wherein the matrix material is nano grain sized.

7. A composite material according to claim 6, wherein the matrix material is less than 100 nm grain sized.

8. A composite material according to claim 1, wherein the matrix material comprises one or more high melting point metals selected from the group including tungsten, molybdenum and alloys thereof.

9. A composite material according to claim 1, wherein the primary and secondary ultra hard or hard particulate materials have an average grain size of 0.1 micron to 100 microns.

10. A composite material according to claim 9, wherein the average grain size of the primary and secondary ultra hard or hard particulate materials is from 10 to 100 microns.

11. A composite material according to claim 9, wherein the average grain size of the primary and secondary ultra hard or hard particulate materials is from 1 to 10 microns.

12. A composite material according to claim 9, wherein the average grain size of the primary and secondary ultra hard or hard particulate materials is from 0.1 to 1 micron.

13. A composite material according to claim 1, wherein the primary and secondary ultra hard or hard particulate materials have an average grain size of less than 0.1 micron.

14. An abrasive insert comprising a layer of polycrystalline diamond (PCD) or polycrystalline cubic boron nitride (PCBN), a substrate; and an interlayer bonding the PCD or PCBN layer to the substrate, wherein the interlayer comprises a composite material as defined in claim 1.

15. An abrasive insert according to claim 9, wherein the substrate is a cemented carbide substrate selected from the group comprising cemented tungsten carbide, cemented tantalum carbide, cemented molybdenum carbide and cemented titanium carbide.

16. An abrasive insert according to claim 9, wherein the cemented carbide further comprises a bonding phase selected from nickel, cobalt, iron or alloys containing one or more of these metals.

17. An abrasive insert according to claim 9, wherein the bonding phase is present in an amount of 6 to 20% by mass.

18. An abrasive insert according to claim 17, wherein the bonding phase of the cemented carbide is less than 6% by mass.

19. A method for producing an abrasive insert according to claim 16, the method including the steps of:
   (1) placing a layer comprising a primary ultra hard or hard particulate material and at least one secondary ultra hard or hard particulate material dispersed in a matrix material on a surface of a cemented carbide substrate,
   (2) placing a layer of diamond or cubic boron nitride particles, optionally with a suitable bonding phase material, on the layer of step (1), creating an unbonded mass, and
   (3) subjecting the unbonded mass to elevated temperature and pressure conditions at which the diamond or cubic boron nitride is crystallographically stable to produce a bonded abrasive insert.

* * * * *